United States Patent [19]

Nestor, Jr. et al.

[11] Patent Number: 4,473,555
[45] Date of Patent: Sep. 25, 1984

[54] NONA- AND DODECAPEPTIDES FOR AUGMENTING NATURAL KILLER CELL ACTIVITY

[75] Inventors: John J. Nestor, Jr., San Jose; John G. Moffatt, Los Altos; John M. Sims, Livermore, all of Calif.

[73] Assignee: Syntex (U.S.A.) Inc., Palo Alto, Calif.

[21] Appl. No.: 542,632

[22] Filed: Oct. 17, 1983

[51] Int. Cl.³ .................... A61K 37/00; C07C 103/52
[52] U.S. Cl. .............................. 424/177; 260/112.5 R
[58] Field of Search .................. 424/177; 260/112.5 R

[56] References Cited
PUBLICATIONS

C. D. Morrow, et al., J. Virology (1983) 429–439, vol. 48, No. 2.

Primary Examiner—Delbert R. Phillips
Attorney, Agent, or Firm—James M. Kanagy; Tom M. Moran

[57] ABSTRACT

The abstract is disclosed herein are nonapeptides and dodecapeptides which augment natural killer cell activity.

6 Claims, No Drawings

NONA- AND DODECAPEPTIDES FOR AUGMENTING NATURAL KILLER CELL ACTIVITY

BACKGROUND OF THE INVENTION

Early work carried out by such investigators as R. Kiessling, R. B. Herberman and R. K. Oldham confirmed the existence of natural cytotoxic reactivity by lymphoid cells taken from human donors. This naturally occurring cell mediated cytotoxicity in vitro has subsequently been investigated and confirmed in the mouse and in humans by the foregoing investigators and others.

The effector cells mediating natural cell mediated cytotoxicity are collectively known as natural killer cells. Natural killer cells were initially defined in a negative way, i.e., as cells lacking some characteristic features of cytotoxic T lymphocytes and other typical T cells, B cells, monocytes or granulocytes. Additional identification work has demonstrated a number of positive features such as, for example, that the natural killer activity is not diffusely distributed among a variety of different types of lymphoid cells but rather is restricted to a discrete subpopulation of cells comprising only 5 to 10 percent of the peripheral blood mononuclear cells. Almost all such cells have also been shown to express receptors for the the Fc portion IgG. Human natural killer cells have also been found to have several other characteristic cell surface markers, including markers that have been closely associated with typical T cells. While these characterizations serve to construct a picture of the natural killer cells a definitive characterization is not presently available.

In addition, the spontaneous appearance of cell mediated cytotoxicity remains undefined. A number of factors have been suggested as the activating mechanism, for example environmental factors such as bacteria parasites, viruses or similar agents have been implicated as causitive agents for the inducement of natural killer cell activity. Genetic factors have also been alleged to play a role in the appearance of natural killer cell activity Another apparently important activator for natural killer cell activity is interferon. Normal mice treated repeatedly with antibodies to interferon have shown a substantial but not complete reduction in their spontaneous natural killer cell activity indicating endogenous interferon may contribute to the spontaneous development of natural killer cell activity.

A representative overview of cell mediated cytotoxicity is given by Herberman, R. B. and R. K. Oldham, Journal of Biological Response Modifiers, 2:111-120 (1983) and Stutman, O. et al, Federation Proceedings, 40 (12):2699 (1981).

This invention relates to nonapeptides and dodecapeptides which are taken in whole or in part from the N-terminus of a polypeptide which is a transcription of a DNA fragment determined to be the producer of the protein portion of human interferon gamma, though the native material, human interferon gamma has not been fully sequenced and identified. It has been determined that the nonapeptide between positions 4 and 12 of the N-terminal portion of this protein augments natural killer cell activity.

SUMMARY OF THE INVENTION

One aspect of this invention relates to nonapeptides and dodecapeptides of the formula X-Asp-Pro-Tyr-Val-Lys-Glu-Ala-Y       (I)

wherein X is N-acyl-Gln, or N-acyl-Cys-Tyr-Cys-Gln- and Y is Gly, Glu, GlyN(R)$_2$ or GluN(R)$_2$ wherein R is hydrogen or alkyl of 1 to 6 carbon atoms and the pharmaceutically acceptable, non-toxic salts thereof.

In a second aspect this invention relates to a method for augmenting natural killer cell cytotoxicity which method comprises administering an effective amount of one or more of the nonapeptides or dodecapeptides in a quantity sufficient to augment natural killer cell activity.

In a third aspect, this invention relates to a pharmaceutical composition comprising one or more of the nonapeptides or dodecapeptides in combination with a pharmaceutically acceptable excipient or a pharmaceutical composition comprising one or more of the nonapeptides or dodecapeptides, a human interferon and a pharmaceutically acceptable excipient.

Specific Embodiments

As set forth above, and for convenience in describing this invention, the conventional abbreviations for the various common amino acids are used as is generally accepted in the peptide art as recommended by the IUPAC-IUB Commission on Biochemical Nomenclature, Biochemistry, 11, 1726 (1972). These represent the L-amino acids, with the exception of the achiral amino acid glycine, and with the further exception of any unatural or natural amino acids which are achiral, or are otherwise designated as D-.

All peptide sequences mentioned herein are written according to the generally accepted convention whereby the N-terminal amino acid is on the left and the C-terminal amino acid is on the right.

It is preferred that the amino acids making up these nonapeptides and dodecapeptides will be the L-configuration for all amino acids having chirality. However, the polypeptides of this invention may be prepared by substituting for one or more L-amino acid residue the corresponding D-amino acid.

The term N-acyl- refers to an functionality wherein the amino nitrogen is bound in an amide linkage to the carboxylic acid residue; said carboxylic acid residue being that of an alkyl carboxylic acid having 1 to 6 carbon atoms or benzoic acid. The abreviation "N-Ac" refers specifically to the N-acetyl radical.

As used herein, the term "pharmaceutically acceptable nontoxic salt" refers to a salt that retains the desired biological activity of tne parent compound and does not impart any undesired toxicological effects. Examples of such a salt is an acid addition salt formed with an inorganic acid, for example hydrochloric acid, hydrobromic acid, sulfuric acid, phosphoric acid, nitric acid and the like; and a salt formed with an organic acid such as for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, naphthalenesulfonic acid, naphthalene disulfonic acids, polygalacturonic acid; a salt formed with polyvalent metal cations such as zinc, calcium, bismuth, barium, magnesium, aluminum, copper, cobalt, nickel, cadmium, and the like; or with an organic cation formed from N,N'-dibenzylethylenediamine or ethylenediamine; or combinations thereof, e.g., a zinc tannate salt and the like.

ASSAY PROCEDURES

The compounds of this invention, including their salts, augment natural killer cell activity.

One measure of such augmentation is to measure the lysis of human myeloid tumor cells designated K562. Lysis is measured by the release of $^{51}$Cr. The assay follows the procedure of Zarling, J. M. et al, Journal of Immunology, 123 (1):63 (1979) or Platsoucas, C. D. et al, Journal of Immunology, 125 (3):1216 (1980).

SYNTHESIS OF PEPTIDES

The polypeptides of the present invention may be synthesized by any techniques that are known to those skilled in the peptide art. An excellent summary of the many techniques so available may be found in Stewart, J. M. and J. D. Young, *Solid Phase Peptide Synthesis*, W. H. Freeman, San Francisco, 1969, and J. Meienhofer, *Hormonal Proteins and Peptides*, Vol. 2, p. 46, Academic Press (New York) 1973 for solid phase peptide synthesis and E. Schroder and K. Lubke, *The Peptides*, Vol. 1, Academic Press (New York) 1965 for classical solution synthesis.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final peptide. By simple modification of this general procedure, it is possible to add more than one amino acid at a time to a growing chain, for example, by coupling (under conditions which do not racemize chiral centers) a protected tripeptide with a properly protected dipeptide to form, after deprotection a pentapeptide.

In addition, it is anticipated that the subject polypeptides may be prepared by recombinant DNA technology, for example by modification and utilization of the DNA sequences coding for interferon-like peptides as disclosed in the laid open European application No. 0,032,134 of Biogen (Derwent No. 53697 D/30) and laid open European patent application No. 0,048,970 of Genentech (Derwent No. 28974 E/15).

PREFERRED EMBODIMENTS

A particularly preferred method of preparing compounds of the present invention involves solid phase peptide synthesis.

In this particularly preferred method the α-amino function of the amino acids is protected by an acid or base sensitive group. Such protecting groups should have the properties of being stable to the conditions of peptide linkage formation, while being readily removable without destruction of the growing peptide chain or racemization of any of the chiral centers contained therein. Suitable protecting groups are t-butyloxycarbonyl (Boc), benzyloxycarbonyl (Cbz), biphenylisopropyloxycarbonyl, t-amyloxycarbonyl, isobornyloxycarbonyl, α, α-dimethyl-3,5-dimethoxybenzyloxycarbonyl, o-nitrophenylsulfenyl, 2-cyano-t-butyloxycarbonyl, 9-fluorenylmethyloxycarbonyl and the like, especially t-butyloxycarbonyl (Boc).

Particularly preferred side chain protecting groups for tyrosine are benzyl, o-bromobenzyloxycarbonyl, 2,6-dichlorobenzyl, isopropyl, cyclohexyl, cyclopentyl and acetyl; for serine: benzyl t-butyl and tetrahydropyranyl.

The C-terminal amino acid is attached to a suitable solid support. Suitable solid supports useful for the above synthesis are those materials which are inert to the reagents and reaction conditions of the stepwise condensation-deprotection reactions, as well as being insoluble in the media used. Suitable solid supports are chloromethylpolystyrene-divinylbenzene polymer, hydroxymethyl-polystyrene-divinylbenzene polymer, and the like, especially chloromethyl-polystyrene-1% divinylbenzene polymer. For the special case where the C-terminus of the compound will be or glycinamide or glutamine amide, a particularly useful support is the benzhydrylamino-polystyrene-divinylbenzene polymer described by P. Rivaille, et al, *Helv. Chim. Acta.*, 54, 2772 (1971). The attachment to the chloromethyl polystyrene-divinylbenzene type of resin is made by means of the reaction of the N α-protected amino acid, especially the Boc-amino acid, as its cesium, tetramethylammonium, triethylammonium, 1,5-diazabicyclo[5.4.0]undec-5-ene, or similar salt in ethanol, acetonitrile, N,N-dimethylformamide (DMF), and the like, especially the cesium salt in DMF, with the chloromethyl resin at an elevated temperature, for example between about 40° and 60° C., preferably about 50° C., for from about 12 to 48 hours, preferably about 24 hours. The N α-Boc-amino acid is attached to the benzhydrylamine resin by means of an N,N'-dicyclohexylcarbodiimide (DCC)/1-hydroxybenzotriazole (HBT) mediated coupling for from about 2 to about 24 hours, preferably about 12 hours at a temperature of between about 10° and 50° C., preferably 25° C. in a solvent such as dichloromethane or DMF, preferably dichlormethane. The coupling of successive protected amino acids can be carried out in an automatic polypeptide synthesizer as is well known in the art. The removal of the N α-protecting groups may be performed in the presence of, for example, a solution of trifluoroacetic acid in methylene chloride, hydrogen chloride in dioxane, hydrogen chloride in acetic acid, or other strong acid solution, preferably 50% trifluoroacetic acid in dichloromethane at about ambient temperature. Each protected amino acid is preferably introduced in approximately 2.5 molar excess and the coupling may be carried out in dichloromethane, dichloromethane/DMF mixtures, DMF and the like, especially in methylene chloride at about ambient temperature. The coupling agent is normally DCC in dichloromethane but may be N,N'-di-iso-propylcarbodiimide or other carbodiimide either alone or in the presence of HBT, N-hydroxysuccinimide, other N-hydroxyimides or oximes. Alternately, protected amino acid active esters (e.g. p-nitrophenyl, pentafluorophenyl and the like) or symmetrical anhydrides may be used.

At the end of the solid phase synthesis the fully protected polypeptide is deprotected and removed from the resin. This is accomplished by treatment with, for example, anhydrous liquid hydrogen fluoride in the presence of anisole or other carbonium scavenger, treatment with hydrogen fluoride/pyridine complex, treatment with tris(trifluoroacetyl)boron and trifluoroacetic acid, by reduction with hydrogen and palladium on carbon or polyvinylpyrrolidone, or by reduction with sodium in liquid ammonia, preferably with liquid hydrogen fluoride, and anisole at a temperature between about −10° and +10° C., preferably about 0° C., for between about 15 minutes and 1 hour, preferably about 30 minutes. The fully deprotected polypeptide is then purified by a sequence of chromatographic steps employing any or all of the following types: ion exchange on a weakly basic resin in the acetate form; hydrophobic adsorption chromatography on underivatized polystyrene-divinylbenzene (for example Amberlite XAD); silica gel adsorption chromatography; ion exchange chromatography on carboxymethylcellulose; partition chromatography, e.g., on Sephadex G-25, or countercurrent distribution; high performance liquid chromatography (HPLC), especially reverse phase HPLC on octyl- or octadecylsilyl-silica bonded phase column packing. This procedure yields a polypeptide with a free carboxylic acid function at the C-terminus when the support in use is derived from a chloromethyl resin (ester linkage) or a C-terminal amide when the support is a benzhydrylamino resin. Substituted amide C-termini, e.g. —NHEt, are prepared by first removing the protected polypeptide from its resin by aminolysis of the ester linkage with the desired amine (e.g. $H_2NEt$) followed by deprotection with the reagents described above, especially liquid HF.

Thus, in another aspect the present invention relates to a method for preparing compounds of the invention and of the pharmaceutically acceptable salts thereof which process comprises:

removing protecting groups and, optionally, covalently bound solid support from a protected polypeptide to afford a compound of Formula (I) or a salt thereof, and optionally (a) converting a compound of Formula (I) to a pharmaceutically acceptable salt, or (b) converting a salt of a compound of Formula (I) to a pharmaceutically acceptable salt, or (c) decomposing a salt of a compound of Formula (I) to a free polypeptide of Formula (I).

The following examples are given to enable those skilled in the art to more fully understand and practice the present invention. They should not be construed as a limitation upon the scope of the invention, but merely as being illustrative and representative thereof.

EXAMPLE 1

In the reaction vessel of a Beckman 990 Peptide Synthesizer is placed 1.0 mmol of Boc-Gly-O-Resin prepared from chloromethylpolystyrene-1%-divinylbenzene resin (1 mmol Cl/g resin) by reaction with Boc-Gly-OCs salt [B. G. Gisin, *Helv. Chim. Acta*, 56, 1476 (1973)]. Amino acids are added sequentially to this resin by means of a synthesis program,

| Step | Action | | Time |
|---|---|---|---|
| 1 | $CH_2Cl_2$ wash | 1 time | 1.5 min |
| 2 | 50% $CF_3CO_2H/CH_2CL_2$ deprotection | 1 time | 1.5 min |
| 3 | 50% $CF_3CO_2H/CH_2CL_2$ deprotection | 1 time | 30 min |
| 4 | $CH_2Cl_2$ wash | 3 times | 1.5 min |

-continued

| Step | Action | | Time |
|---|---|---|---|
| 5 | 10% triethylamine/$CH_2CH_2$ | 2 times | 1.5 min |
| 6 | $CH_2Cl_2$ wash | 3 times | 1.5 min |
| 7 | Nα-Boc-amino acid solution | 1 time | add |
| 8 | N,N′—dicyclohexylcarbodiimide solution | 1 time | add |
| 9 | $CH_2Cl_2$ rinse and hold - reaction coupling | 1 time | 2 hr |
| 11 | $CH_2Cl_2$ wash | 3 times | 1.5 min |
| 12 | ethanol wash | 3 times | 1.5 min |
| 13 | $CH_2Cl_2$ wash | 3 times | 1.5 min |

Steps 1-13 complete a coupling cycle for one amino acid and completeness of the reaction is checked by the ninhydrin method of E. Kaiser, et al., *Anal. Biochem.*, 34, 595 (1970).

The resin is coupled sequentially with a 2.5 molar excess of each protected amino acid and DCC. Thus, the resin is treated during successive coupling cycles with 0.473 g of Boc-Ala-OH;
0.843 g of Boc-Glu(OBzl)-OH;
0.951 g of Boc-Lys(Z)-OH;
0.543 g of Boc-Val-OH;
0.703 g of Boc-Tyr-OH;
0.538 g of Boc-Pro-OH;
0.806 g of Boc-Asp(OBzl)-OH;
0.616 g of Boc-Gln-OH and 0.51 g of 1-hydroxybenzotriazole; and
3.0 ml of $Ac_2O$.

The resin is removed from the reaction vessel, washed with $CH_2Cl_2$, and dried in vacuo to yield 1.5 g of the protected polypeptide resin.

The polypeptide product is simultaneously removed from the resin and completely deprotected by treatment with anhydrous liquid HF. A mixture of 1.5 g of protected polypeptide resin and 2 ml of anisole (scavenger) in a Kel-F reaction vessel is treated with 20 ml of redistilled (from $CoF_3$) anhydrous liquid HF at 0° C. for 1 hour. The HF is evaporated under vacuum and the residue of Ac-Gln-Asp-Pro-Tyr-Val-Lys-Glu-Ala-Gly-OH, as its HF salt, is washed with ether. The residue is then extracted with glacial acetic acid. The acetic acid extract is lyophilized to yield 0.725 g of crude material.

Purification is achieved by preparative high performance liquid chromatography on a 150 mg sample using a 2.5×100 cm column of 20-40 micron octadecylsilylated silica (Merck Lichroprep $C_{18}$) The eluent is 91% 0.03 M $NH_4OAc$/9% acetonitrile. In 4 runs a total of about 600 mg of crude material is purified. After three lyophilizations from water, 260 mg of pure Ac-Gln-Asp-Pro-Tyr-Val-Lys-Glu-Ala-Gly-OH is obtained as its acetic acid salt $[\alpha]_D^{25} -73.3°$ (c 1, HOAc).

EXAMPLE 2

A. A solution of 0.1 g of the hydrogen fluoride salt of Ac-Gln-Asp-Pro-Tyr-Val-Lys-Glu-Ala-Gly-OH (See Example 1) is dissolved in 50 mL of water and passed through a column of 50 g Dowex 3 anion exchange resin which had previously been equilibrated with acetic acid and washed with deionized water. The column is eluted with deionized water and the effluent is lyophilized to yield the corresponding acetic acid salt of Ac-Gln-Asp-Pro-Tyr-Val-Lys-Glu-Ala-Gly-OH.

Repeating the above, substituting other acids for acetic acid during the equilibration of the resin, there may be obtained, for example, the corresponding salts with hydrochloric acid, hydrobromic acid, sulfuric acid, phosphoric acid, nitric acid, benzoic acid, and the like.

Similarly there may be prepared the acid addition salts of the other peptides described herein.

B. In the case of salts of low water solubility, these may be prepared by precipitation from water utilizing the desired acid. For example:

Zinc tannate salt—a solution of 10 mg of Ac-Gln-Asp-Pro-Tyr-Val-Lys-Glu-Ala-Gly-OH acetic acid salt in 0.1 mL of water was treated with a solution of 8 mg of tannic acid in 0.08 mL of 0.25 M NaOH. A solution of 5 mg of ZnSO4 heptahydrate in 0.1 mL of water was immediately added to the polypeptide solution.

The resultant suspension was diluted with 1 mL water and the precipitate was centrifuged. The supernatant was decanted and the residue was washed twice with 1 mL portions of water by centrifugation of the precipitate and decantation of the supernatant. The precipitate was dried in vacuo to yield 15 mg of the mixed zinc tannate salt of the above named nonapeptide.

Pamoate salt - to a solution of 0.05 mg Ac-Gln-Asp-Pro-Tyr-Val-Lys-Glu-Ala-Gly-OH acetic acid salt in a mixture of 1.6 mL of ethanol and 0.1 mL of 0.025 mml M NaOH was added solution of 11 mg of pamoic acid in 0.3 mL of 0.25 M NaOH. The solvents were removed at reduced pressure and the residue was suspended in 2 mL of water, centrifuged, and the supernatant was decanted. The precipitate was washed with 1.5 mL H2O, centrifuged, and the supernatant was decanted. The precipitate was dried in vacuo to yield 54 mg of the pamoate salt of the above named nonapeptide.

In a similar manner other salts of low water solubility may be prepared.

C. Preparation of acid addition salt from free peptide.

To a solution of 50 mg of Ac-Gln-Asp-Pro-Tyr-Val-Lys-Glu-Ala-Gly-OH as the free base is added 30 mL of 1N acetic acid. The resulting solution is lyophilized to yield 50 mg. of the acetic acid salt of the above.

Similarly, replacing acetic acid with other acids (in stoichiometrically equivalent amounts relative to peptide) there was obtained other acid addition salts of the peptides herein, for example, the salts with hydrochloric acid, hydrobromic acid, sulfuric acid, phosphoric acid, nitric acid.

D. Preparation of salt with metal cation, e.g., zinc salt.

To a solution of 50 mg Ac-Gln-Asp-Pro-Tyr-Val-Lys-Glu-Ala-Gly-OH acetic acid salt in a mixture of 0.4 mL of 0.25 M NaOH, 0.3 mL water, and 1 mL ethanol was added a solution of 15 mg of ZnSO4 heptahydrate in 0.2 mL of water. The precipitate was centrifuged and the supernatant was decanted. The precipitate was washed with 1 mL of water by centrifugation and decantation of the supernatant. The precipitate was dried in vacuo to yield 48 mg of the zinc salt of the above named nonapeptide.

In a similar manner salts with other multivalent cations e.g. calcium, bismuth, barium, magnesium, aluminum, copper, cobalt, nickel, cadmium and the like, may be prepared.

EXAMPLE 3

A solution of 50 mg of Ac-Gln-Asp-Pro-Tyr-Val-Lys-Glu-Ala-Gly-OH water is passed through a 50 mm column of Dowex 1 (strongly basic, quaternary ammonium anion exchange resin) which had been equilibrated with NaOH solution to make the counter ion hydroxide. The column is eluted with 150 ml of water and the eluant is lyophilized to yield 45 mg of the corresponding polypeptide as the free base.

Similarly other acid addition salts of compounds of the peptides herein, e.g., those mentioned in Example 2, may be converted to the corresponding free bases.

EXAMPLE 4

The following are typical pharmaceutical compositions containing, as active ingredient, a polypeptide of the present invention, for example Ac-Gln-Asp-Pro-Tyr-Val-Lys-Glu-Ala-Gly-OH by itself or as a pharmaceutically acceptable salt, e.g., the acetic acid addition salt, the zinc salt, the zinc tannate salt, etc.

A. Tablet formulations for buccal (e.g. sublingual) administration:

| | | |
|---|---|---|
| 1. | Polypeptide | 10.0 mg |
| | Compressible Sugar, USP | 86.0 mg |
| | Calcium Stearate | 4.0 mg |
| 2. | Polypeptide | 10.0 mg |
| | Compressible Sugar, USP | 88.5 mg |
| | Magnesium Stearate | 1.5 mg |
| 3. | Polypeptide | 5.0 mg |
| | Mannitol, USP | 83.5 mg |
| | Magnesium Stearate, USP | 1.5 mg |
| | Pregelatinized Starch, USP | 10.0 mg |
| 4. | Polypeptide | 10.0 mg |
| | Lactose, USP | 74.5 mg |
| | Pregelatinized Starch, USP | 15.0 mg |
| | Magnesium Stearate, USP | 1.5 mg |

What is claimed is:

1. A compound of the formula $$X\text{-Asp-Pro-Tyr-Val-Lys-Glu-Ala-}Y \qquad (I)$$

wherein X is N-acyl-Gln, or N-acyl-Cys-Tyr-Cys-Gln- and Y is Gly, Glu, GlyN(R)$_2$ or GluN(R)$_2$ wherein R is hydrogen or alkyl of 1 to 6 carbon atoms and the pharmaceutically acceptable, non-toxic salts thereof.

2. A compound of claim 1 wherein X is a N-Ac-Gln and Y is Gly, namely N-Ac-L-Gln-L-Asp-L-Pro-L-Tyr-L-Val-L-Lys-L-Glu-L-Ala-Gly and the pharmaceutically acceptable non-toxic salts thereof.

3. A compound of claim 1 wherein X is N-Ac-Gln and Y is L-Glu, namely N-Ac-L-Gln-L-Asp-L-Pro-L-Tyr-L-Val-L-Lys-L-Glu-L-Ala-L-Glu and the pharmaceutically acceptable non-toxic salts thereof.

4. A compound of claim 1 wherein X is N-Ac-L-Cys-L-Tyr-L-Cys-L-Gln and Y is Gly, namely N-Ac-L-Cys-L-Tyr-L-Cys-L-Gln-L-Asp-L-Pro-L-Tyr-L-Val-L-Lys-L-Glu-L-Ala-Gly and the pharmaceutically acceptable non-toxic salts thereof.

5. A compound of claim 1 wherein X is N-Ac-L-Cys-L-Tyr-L-Cys-L-Gln and Y is Glu, namely N-Ac-L-Cys-L-Tyr-L-Cys-L-Gln-L-Asp-L-Pro-L-Tyr-L-Val-L-Lys-L-Glu-L-Ala-L-Gln and the pharmaceutically acceptable non-toxic salts thereof.

6. A pharmaceutical composition for augmenting natural killer cell activity comprising an effective amount of a compound of claim 1 in admixture with at least one pharmaceutically acceptable excipient.

* * * * *